May 16, 1967 A. MARZILLI ET AL Plant Pat. 2,743
DOGWOOD TREE
Filed June 14, 1965
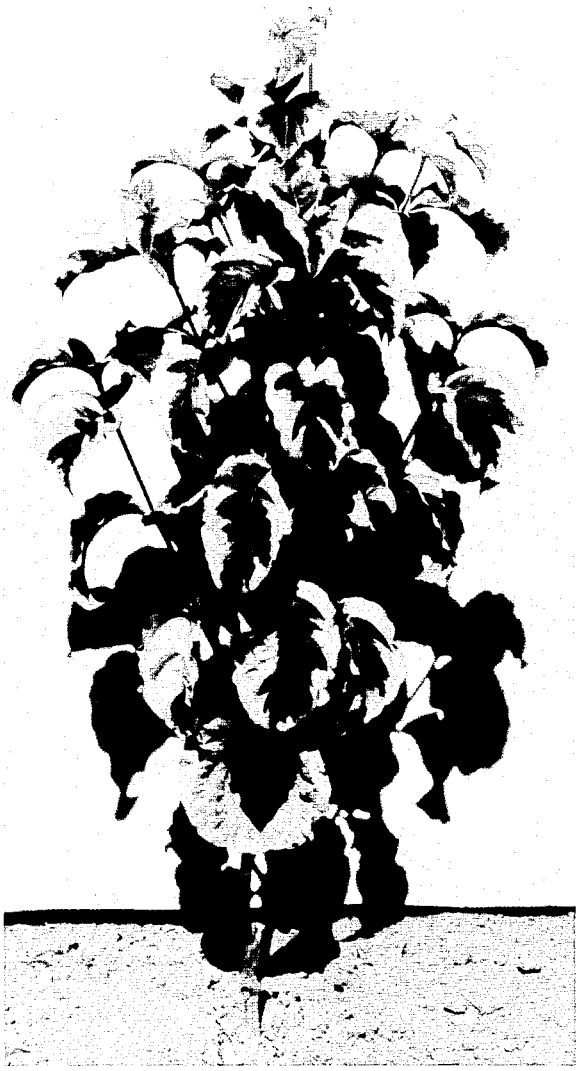
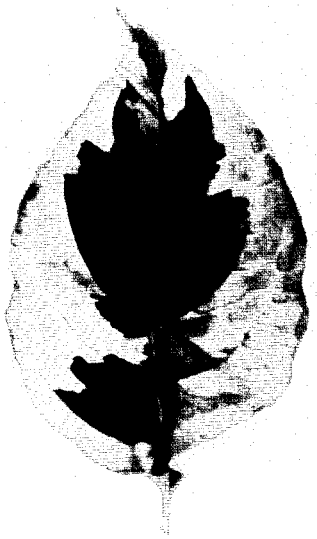
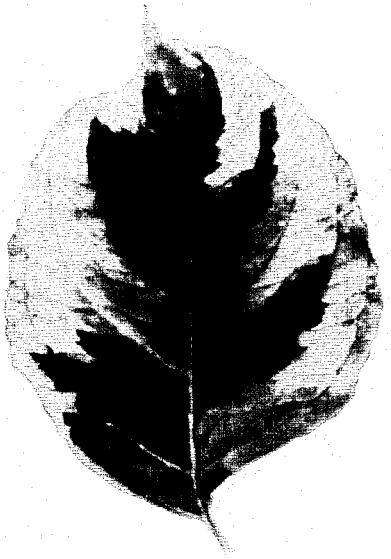
BUCKHORN, BLORE, KLARQUIST, & SPARKMAN
ATTORNEYS
ARMOND MARZILLI
JOHN FRANK SCHMIDT, JR.
INVENTORS United States Patent Office Plant Pat. 2,743
Patented May 16, 1967

2,743
DOGWOOD TREE

Armond Marzilli, Canton, Ohio, and John Frank Schmidt, Jr., Troutdale, Oreg.; said Marzilli assignor of one-half to John C. Marzilli, Canton, Ohio Filed June 14, 1965, Ser. No. 463,976
1 Claim. (Cl. Plt.—51)

The present invention relates to a new and distinct variety of dogwood tree, believed to be of a variety of *Cornus florida.*

The primary distinguishing characteristic of our variety of dogwood tree is its multi-colored leaf.

Our new variety of dogwood tree was found by Armond Marzilli on his residential lot at 5433 Everhard Drive, Northwest, Canton, Ohio, at a place between his garage and house and close to the driveway. The tree had been at such location for some time when it was run over by a truck and broken. Armond Marzilli cut off the broken and damaged parts and left the remainder. In the multiple growth that resulted, one of the stems had multi-colored leaves as described herein and such stem resulted in the parent tree from which trees like that in the accompanying drawings were produced.

John Frank Schmidt, Jr. reproduced at his nursery near Troutdale, Ore., the new variety, asexually, and specifically by obtaining buds from the parent tree and budding the same onto *Cornus florida* seedlings in accordance with budding procedures known to him. After the budding had taken, the part of the seedling stock above the bud was removed. The characteristics of our tree have proved to be firmly fixed.

FIG. 1 is a colored photograph of a tree of our invention taken around the end of August or early in September 1964;

FIG. 2 is a color photograph of a leaf of the tree (or a similar tree) shown in FIG. 1, the leaf being from the middle outside part of the tree;

FIG. 3 is a color photograph of a leaf of the tree of FIG. 1 (or a similar tree) taken from a shaded (interior) portion of the tree to show the effect of the absence of sunlight on the leaf.

Referring to the drawings, it is evident from FIGS. 1 and 2 that the leaves of our tree in autumn color are not only multi-colored but that the areas of darker coloration are centrally oriented and furthermore that there is a "leaf within a leaf" effect. Still further the darker areas of coloration are distinctly defined and in many places terminate at vein lines. It is further evident that the darker areas vary in form and shape from leaf to leaf but in general terminate short of the side edges of the leaf. The darker areas appear in the spring dark green in color surrounded or positioned on a matrix of lighter green. Thereafter, as the leaves age, portions of the darker green areas turn deeper green and then greenish-purple, while the lighter green areas turn medium and light yellow and some of the latter areas then turn reddish and the transition is varied so that it is not uncommon for a single leaf to have at the same time areas of deep green or deep greenish-purple, yellow, green and red. As the leaves age still more, the dark green-purple areas turn into deeper purple, the light green disappears and the leaf is then green-purple with red and yellowish or tannish areas. Since the new leaves at the top of the tree of our invention commence their color change later than the older leaves, the tree at certain stages will have some essentially two-color leaves at the top, three-color leaves near the top and lower, three and four color leaves in the middle zone and lower areas, and two and three color leaves near the bottom. Thus, a tree with strikingly colored leaves is produced. It is pointed out that while the darker areas of a leaf of our tree are sharply delineated, and the lines delineating the darker areas do not shift, and thus the relative sizes of the darker and lighter areas remain constant, each area increases in absolute size during growth of the leaf. The various color zones of the lighter area are not sharply delineated from one another, but to the contrary merge into one another and their relative sizes change, some increasing in relative size while others decrease.

Our tree differs from other *Cornus florida* and other dogwood trees as follows:

The leaf of the *Cornus florida* is green in the spring and gradually darkens and turns purple-green in the fall. In fact, the color of the *Cornus florida* leaf is substantially the same and goes through the same color changes as does the inside darker area of the leaf of our tree. The flowers on the tree are white. The flowers on our tree are white and the bark and other physical aspects are similar or almost identical to that of the *Cornus florida.* However, the leaves of our tree, insofar as color is concerned, are strikingly different from those of the *Cornus florida* as is evident from the above description.

The *Cornus welchii* has a variegated leaf, but the *welchii* is a poor grower and its leaves are heavily wrinkled at the edges almost as if they were gathered. Also, the coloration of the *welchii* leaves is different in that in the *welchii* the leaf is blotched over with greens against cream or white areas.

Our tree in contrast to the *Cornus welchii* is a fast and strong grower and its growth habits are very much like and almost identical to that of the *Cornus florida.* For instance, in one year our tree will grow from thirty to thirty-six inches from a bud on *Cornus florida* stock.

The tartarian dogwood has a variety *spaethii* with leaves edged with yellow, and a variety *argenteo-marginata* with leaves edged with creamy-white. The coloration of these leaves is distinctly different from that of our variety. The bloodtwig dogwood *Cornus sanguinea* includes a variety *variegata* which has leaves variegated with yellowish-white but the coloration of this leaf is obviously different from the leaf of our tree as is evident from the coloration described above.

Following is a brief description of our new variety tree, color terminology being in accord with the 1950 edition of "Dictionary of Color" by Maerz and Paul. It is pointed out however that the colors indicated below are only approximate, because the coloring of the leaves varies considerably as the leaves age and depends on the amount of sunlight the leaves receive.

Tree: Upright, healthy.

Growth: Rapid and vigorous, attaining a height of two to three feet at one year from budding onto a *Cornus florida* seedling. The growth is similar to that of the *Cornus florida.*

Trunk: Similar in shape, coloration and form and has the appearance of that of the *Cornus florida.*

Foliage: Size and shape—similar to that of the *Cornus florida.*

Color: As described above and more specifically (a) centrally oriented darker areas—initially a green (not found in Maerz and Paul color dictionary, but similar to Plate 18, blocks G7–11) and like the initial color of the *Cornus florida* at the same stage of development. This color gradually deepens until it assumes a coloration also evidently not shown in the Maerz and Paul color dictionary, but somewhat like that of Plate 24, blocks E7–11, with the leaves eventually assuming a purplish tinge (not found in Maerz and Paul but similar to the color of the *Cornus florida* leaf at the same stage of development); (b) matrix or surrounding areas initially are light green similar to the color shown at Plate 18, blocks K3–6. This color changes over the season to a yellow something like Plate 10, blocks L2–6. Then portions of the yellow area turn rose colored on the order of Plate 3, blocks L6–7.

Having thus described our invention we claim:

A new and distinct variety of dogwood tree substantially as herein shown and described, characterized particularly as to novelty by having leaves similar in shape, size and form to those of the *Cornus florida* but of multicolor form and at certain stages having three or four colors, and particularly characterized by a darker, sharply defined color area basically centrally oriented in the leaf and surrounded by lighter, multi-colored matrix.

No references cited.

ABRAHAM G. STONE, *Primary Examiner.*

ROBERT E. BAGWILL, *Examiner.*